United States Patent

Tallarida

[11] Patent Number: 5,906,596
[45] Date of Patent: May 25, 1999

[54] PERCUTANEOUS ACCESS DEVICE

[75] Inventor: Steven J. Tallarida, Mansfield, Mass.

[73] Assignee: STD Manufacturing, Stoughton, Mass.

[21] Appl. No.: 08/774,923

[22] Filed: Dec. 27, 1996

Related U.S. Application Data

[63] Continuation-in-part of application No. 08/756,235, Nov. 26, 1996, abandoned.

[51] Int. Cl.⁶ ..................................................... A61M 5/32
[52] U.S. Cl. ............................................ 604/175; 604/93
[58] Field of Search ................................ 604/49, 51, 52, 604/93, 174, 175, 890.1, 891.1

[56] References Cited

U.S. PATENT DOCUMENTS

| | | | |
|---|---|---|---|
| 4,311,148 | 1/1982 | Courtney et al. | 604/175 |
| 4,533,349 | 8/1985 | Bark | 604/174 |
| 4,645,492 | 2/1987 | Weeks | 604/174 |
| 4,673,394 | 6/1987 | Fenton, Jr. et al. | 604/175 |
| 4,886,501 | 12/1989 | Johnston et al. | 604/93 |
| 4,897,081 | 1/1990 | Poirier et al. | 604/175 |
| 5,108,377 | 4/1992 | Cone et al. | 604/93 |
| 5,167,638 | 12/1992 | Felix et al. | 604/175 |
| 5,318,545 | 6/1994 | Tucker | 604/244 |
| 5,399,168 | 3/1995 | Wadsworth, Jr. et al. | 604/175 |
| 5,405,325 | 4/1995 | Labs | 604/93 |
| 5,527,278 | 6/1996 | Ensminger et al. | 604/93 |
| 5,613,945 | 3/1997 | Cai et al. | 604/93 |
| 5,628,780 | 5/1997 | Helland et al. | 604/174 |

FOREIGN PATENT DOCUMENTS 0472618   11/1995   European Pat. Off. ........ A61M 39/02

*Primary Examiner*—Corrine McDermott
*Attorney, Agent, or Firm*—Hayes, Soloway, Hennessey, Grossman & Hage, P.C.

[57] ABSTRACT

A subcutaneous access port for surgical implantation in the body of a mammal, such access port comprising a body portion defining a chamber with an open face, the body portion having attached thereto a biocompatible mesh material, whereby the subcutaneous access port may be fixed within the body by suturing or surgical stapling through the biocompatible mesh material.

38 Claims, 1 Drawing Sheet

PERCUTANEOUS ACCESS DEVICE

CROSS-REFERENCE TO RELATED APPLICATIONS

This application is a continuation-in-part of U.S. application Ser. No. 08/756,235, filed Nov. 26, 1996 now abandoned.

FIELD OF THE INVENTION

The present invention describes a general system and method for implanting medical devices in the body of a patient. The invention has particular utility in connection with devices for permitting access to the body through the skin, e.g. percutaneous/subcutaneous devices, and more specifically, to skin penetration devices which may be used as an access port into the body for extended periods of time, and will be described in connection with such utility, although other utilities are contemplated. In such embodiment, the invention comprises a subcutaneous access port for vascular access, utilizing, in lieu of standard sutures, an implantable integral fabric of biocompatible material which may be sutured or stapled into place, and the implantable fabric may be integral to a corresponding medical device or placed over said device to retain it in the body.

BACKGROUND OF THE INVENTION

The prior art is replete with numerous disclosures directed to percutaneous access/subcutaneous devices. As disclosed therein, such devices are useful when frequent or long-term access to the body is required, as in kidney dialysis, drug delivery, intravenous feeding, ostomies, and transmission of energy to intracorporeal or blood pumps. Typically, such access port devices are surgically implanted under the skin and generally include an outlet opening connected by means of a tubular conduit (catheter) system to a blood vessel within the body.

For example, in U.S. Pat. No. 5,527,278, there is described an access port for implantation within the body of a patient for providing repeated access to a specific site within the patient and communicating with the site by an implanted internal catheter. The access port includes a housing having an inlet orifice leading to a reduced diameter guide passageway. An external filament such as a needle, guidewire, optical fiber external catheter can be introduced into the access device, and fed through the housing. This system is said to allow for the introduction of therapeutic agents, the removal of fluids from the body, or the introduction of sensing and articulating devices to the specific site within the patient.

In U.S. Pat. No. 5,399,168, there is described a subcutaneous implantable access port formed of a housing having a pair of non-circular fluid cavities enclosed therein by a floor, walls upstanding from the floor, and a self-sealing septum system above each fluid cavity. The access ports thereby provide a plurality of needle-penetrable, self-sealing septums, each affording repeated access to a corresponding plurality of distinct fluid cavities each in communication with a plural lumen catheter.

In U.S. Pat. No. 5,167,638, there is reported a multi-chamber subcutaneously implantable infusion port and catheter assembly formed from a small number of plastic components that are easily injection molded and assembled. The components are constructed so that a catheter assembly is easily and securely bonded to the port. In addition, the '638 patent makes reference to the fact that the access port has an anchoring base made of flexible biocompatible materials such as silicon rubber.

In U.S. Pat. No. 4,897,081 there is disclosed a percutaneous access device (PAD) for long term skin penetration and use as an access port in the body of a patient. The PAD is said to include a flat flange or skirt, formed from a semiflexible material such as a semirigid polyurethane. The skirt contains on its surface two "stages" or regions of biocompatible material. The first stage is described to be of biocompatible polytetrafluoroethylene (PTFE) having pore sizes of about 50–125 microns and a thickness of about 0.020 inches. Optional to PTFE, it is suggested that one can employ a polyurethane, such as "Tecoflex" filaments, which are said to have excellent cell attachment characteristics. The second stage is described as a dacron polyester woven fabric with loose strands to allow for cell infiltration. The '081 patent goes on to emphasize that there is a downgrowth of epidermal cells through the first stage and the formation of mature collagen in the second stage.

Attention is also directed to U.S. Pat. No. 5,318,545, which describes a composite implantable biocompatible vascular access port for delivering a fluid medication, and U.S. Pat. No. 5,405,325, which discloses an areterial access port which is grafted directly into the vascular system. In addition, European Patent Application No. 90908334 describes an implantable vascular access device which includes a port said to be made of a biocompatible housing, and a septum which is also said to include a biocompatible, self-resealing, penetrable material.

However, as can be seen upon review of the above prior art, a significant drawback of the presently available skin penetration devices relates to the difficulty of attaching said devices by standard suturing procedures. Typically, in the skirt which surrounds the access devices of the prior art, small openings are provided to allow for anchoring of the PAD or subcutaneous device to the patient. This is best illustrated in U.S. Pat. No. 4,673,393, which emphasizes that the PAD housing contains in the skirt or flange section thereof evenly spaced apertures which provides an opening that must be aligned with the suture needle for suturing the device to a layer of tissue when implanting. Accordingly, in the suturing of such devices, the physician has to make absolutely certain that suturing proceeds through these limited openings in order to guarantee that the PAD/subcutaneous device will be immobilized in the desired location. That being the case, current PAD/subcutaneous designs do not readily permit an easy and convenient method for implanting the PAD or subcutaneous device at a desired location within the body.

Accordingly, it is an object of this invention to provide an improved percutaneous/subcutaneous access device, for vascular access, utilizing in lieu of standard sutures, an implantable, integral fabric, mesh material or perforated film of polymer or other biocompatible material. The material may be readily sutured or stapled into place at any position thereof without the need for surgical needle alignment, as noted above, and the implantable fabric can be integral to the device or placed over the device to retain it in the body.

It is also an object of this invention to provide a design configuration while having specific utility for the placement of a PAD or subcutaneous device, further provides a convenient method for immobilizing other types of medical devices in the body, such as a pacemaker.

SUMMARY OF THE INVENTION

A percutaneous/subcutaneous access port for surgical implantation in the body of a mammal, such access port comprising a body portion defining a chamber with an open face, said body portion having attached thereto a biocompatible mesh material, said biocompatible mesh material implantable via suturing or surgical stapling. A key feature of such percutaneous/subcutaneous access port design is that the biocompatible mesh material is easy to handle and allows for suturing or stapling of the device into place by suturing or stapling along any section of the mesh material thereof. Accordingly, staples or sutures through the biocompatible mesh material secure the subcutaneous port at a desired location within the body, in addition to providing the appropriate porosity so that a dermal/biomaterial interface can be formed, promoting a biological seal along the entire surface of the biocompatible mesh employed.

Furthermore, it is to be noted that in method form, the present invention provides a method of providing repeated access to a preselected site within a patient by an external filament such as an external catheter, needle, wire or optical fiber, comprising the steps of providing a subcutaneous access port said port comprising a body portion defining a chamber with an open face, said body portion having attached thereto a biocompatible mesh material, making an incision in a patient's skin, and locating said access port to a desired location and affixing said access port at said desired location via suturing or stapling through said mesh material, and closing the incision.

BRIEF DESCRIPTION OF THE DRAWINGS

FIG. 1 is a side view of the preferred percutaneous access device (PAD) described wherein.

DESCRIPTION OF THE PREFERRED EMBODIMENTS

Figure 1:
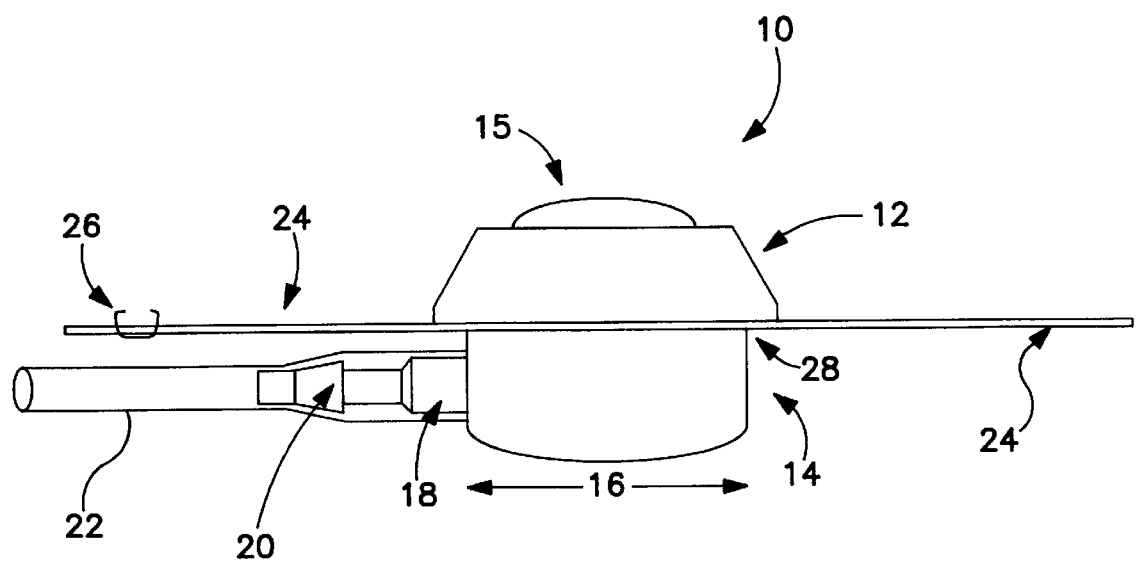
Figure 2:
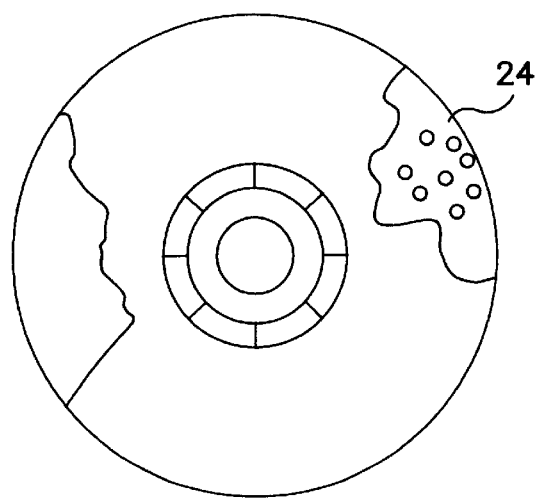
FIG. 2 is a top plan view of the PAD of FIG. 1.

FIGS. 1 and 2 illustrate the percutaneous access device in accordance with the present invention. As shown therein, the PAD device 10 comprises, in a preferred embodiment, a titanium cap 12 and a titanium port section 14, and a septum 15, the septum being manufactured from a silicon type polymer resin. In addition, the cap and port section, while preferably titanium, may be manufactured from non-metallic materials, such as a plastic or elastomeric material, such as a polyacetal resin, sold under the tradename DELRIN®.

The port 14, as measured by line 16, is preferably 0.75 inches in diameter, but can range from 0.10 to 0.35 inches. The port section also preferably has a depth of about 0.10 to 0.25 inches. Attached to the port section 14 is a catheter stem 18 with an end section 20 releasably securing a catheter 22 to said end section thereof.

At 24 the biocompatible mesh material is shown, which as illustrated in side view, projects outwardly from the PAD or subcutaneous device and is preferably located and secured between the cap 12 and port sections 14. Those skilled in the art will recognize that the mesh material should be of such type which allows for penetration of a needle or other type of suturing instrumentality so that the mesh material can be conveniently sutured or stapled into place, along any section of the mesh material thereof. Accordingly, when such suturing or stapling procedure takes place, the medical practitioner does not need to insure that the needle or staple aligns precisely with a preformed opening on the flange or skirt of the PAD or subcutaneous device, which thereby eliminates the often time-consuming difficulties associated with such prior art alignment procedures. As noted, the mesh material itself can be sutured or stapled at any position along section 24 (see item 26, which illustrates a typical staple placement for stapling into the subcutaneous tissue) and a much quicker and facile implantation technique can be obtained according to the teachings of the present invention. In addition, the staple 26 which staples into the subcutaneous tissue, is preferably manufactured from titanium or a bioadsorbable material.

In a particular preferred embodiment, the mesh material 24 projects outwardly for a distance of 0.1 to 4.0 inches, and is disk shaped, with a thickness in the range of about 0.001 to 0.060 inches, and with a pore size in the range $1 \times 10^{-6}$ to 0.25 inches. In addition, the mesh material is preferably selected from the group consisting of synthetic polymeric fiber material, perforated film and stainless steel. The polymeric fiber materials themselves are preferably selected from the group consisting of polyolefin fibers, such as polypropylene, and other types of biocompatible resins, such as polytetrafluroethylene. The perforated film is similarly selected from the group consisting of polytetrafluroethylene, biocompatible polymer, stainless steel or titanium. The biocompatible mesh material is preferably attached to the PAD by an adhesive such as silicon or other biocompatible adhesive, which secures the mesh material to the surfaces of the cap 12 and port 14, in the region 28, as shown in FIG. 1. Alternatively, the mesh material can be crimped onto the PAD or subcutaneous device, and such crimping can also take place at region 28, again between the cap and port sections.

In addition to providing the advantageous attachment procedure detailed above, the design herein also provides, via the biocompatible mesh material, the opportunity for the formation of a dermal/biomaterial interface which forms as between the biocompatible mesh material and the subcutaneous tissue. That is, a characteristic of the biocompatible mesh material is that such material, as a consequence of its porosity, allows for the downgrowth of epidermal cells, which thereby assist in formation of a biological seal as between the device and adjoining tissue. Accordingly, in addition to providing a much easier attachment procedure, the devices herein disclosed are also medically more efficient in connection with the seal that is ultimately formed.

Furthermore, material 24 may optionally include non-porous material, which is still biocompatible, but additionally characterized in that such non-porous material actually precludes the downgrowth of epidermal cells mentioned above. In such optional embodiment, it will be appreciated that removal of the PAD subcutaneous port will be more readily accomplished as cellular interpenetration will be avoided. In such alternative embodiment, the non-porous material 24 again preferably projects outwardly for a distance of 0.1 to 4.0 inches, and is disk shaped, with a thickness in the range of about 0.001 to 0.060 inches. In such regard, various non-porous polymeric film materials are particularly preferred, including, e.g., polysiloxanes, nylon type elastomers, polyester based elastomers, polyolefine based elastomers, polyurethanes, polytetrafluroethylene, and/or stainless steel, titanium or other metal. In general, however, any non-porous film-forming type material will be suitable in this optional embodiment, which film material is also preferably flexibile, thereby allowing for ease of positioning, together with ease of suturing and stapling, and as noted, ease of removal.

Furthermore, in the case of metalic film material, it is to be noted that in general, a thickness of about 0.0001–0.020 inches will be suitable for the purposes of the present invention. Preferably, however, the metalic film thickness is about 0.002–0.010 inches, and in a most preferred embodiment, the metalic film material will be about 0.002–0.005 inches in thickness.

It will be appreciated that the design herein not only provides a convenient method for securing a medical device such as a subcutaneous access port, but also serves as a significant improvement for the placement (suturing or stapling) of any type of medical device within a patient's body. For example, when a heart pacemaker must be installed, the types of problems noted above are again presented, as the surgeon must insure that the suture needle passes within those apertures normally present in the pacemaker which apertures are designed for anchoring the pacemaker with the suture filaments. Accordingly, in such a case, and pursuant to the teachings of the present invention, the apertures can be eliminated, and the pacemaker can now be more conveniently attached to a biocompatible mesh material as described herein, which is attached to the pacemaker, thereby providing the surgeon a much easier target for locating and suturing (or stapling) the pacemaker into the patient.

The invention may be embodied in other specific forms without departing from its spirit or essential characteristics. Thus, the described embodiments are to be considered in all respects only as illustrative and not restrictive. The scope of the invention is, therefore, indicated by the appended claims rather than by the foregoing description, and all changes which come within the meaning and range of equivalency of the claims are to be embraced within their scope.

What is claimed is:

1. A medical device for surgical implantation in the body of a mammal which does not require alignment for suturing/stapling through a preformed opening, said device having attached thereto and projecting outwardly from an access port a single layer of biocompatible mesh material, wherein said mesh material contains pores of sufficient size over the entirety of said biocompatible mesh material's surface to allow suturing or stapling through any portion of said mesh material, whereby said device may be fixed within a body via suturing or surgical stapling through said biocompatible mesh material.

2. A percutaneous/subcutaneous access port for surgical implantation in the body of a mammal which does not require alignment for suturing/stapling through a preformed opening, such access port comprising a body portion defining a chamber with an open face, said body portion having attached thereto a biocompatible mesh material wherein said biocompatible mesh material consists essentially of a single layer of mesh material having a surface with pores therethrough wherein said pores are of sufficient size and are present over the entirety of said biocompatible mesh material's surface to allow suturing or stapling through any portion of said mesh material, whereby said subcutaneous access port may be fixed within a body via suturing or surgical stapling through said biocompatible mesh material.

3. The access port of claim 2, wherein said biocompatible mesh material is selected from the group consisting of synthetic polymeric fiber material, perforated film, and stainless steel.

4. The access port of claim 3 wherein said biocompatible mesh material comprises a synthetic polymeric fiber material selected from the croup consisting of polypropylene and poly(tetrafluoroethylene).

5. The access port of claim 3, wherein the biocompatible mesh material comprises a perforated film selected from the group consisting of polytetrafluoroethylene, stainless steel and titanium.

6. The access port of claim 2, wherein said biocompatible mesh material is attached to said access port by an adhesive.

7. The access port of claim 6, wherein the adhesive is a biocompatible adhesive.

8. The access port of claim 7 wherein the adhesive is a silicon adhesive.

9. The access port of claim 2, wherein said access port comprises metallic material.

10. The port of claim 2, wherein said biocompatible mesh material is disk-shaped and has a thickness in the range of about 0.005 to 0.060 inches, and a diameter in the range of about 0.10 to 4.0 inches.

11. The access port of claim 2, wherein the biocompatible mesh material has a pore size in the range of $1 \times 10^{-6}$ to 0.250 inches.

12. The access port of claim 2, wherein said access port comprises a non-metallic material.

13. The access port of claim 12 wherein said non-metallic access port comprises a plastic or elastomeric material.

14. A percutaneous/subcutaneous access port for surgical implantation in the body of a mammal, such access port comprising a body portion defining an upper cap portion containing a chamber with an open face, said body portion having a lower port section and attached thereto a biocompatible mesh material wherein said mesh material contains pores of sufficient size to allow suturing or stapling through any portion of said mesh material, whereby said subcutaneous access port may be fixed within a body via suturing or surgical stapling through said biocompatible mesh material and wherein said access port further contains a crimper on said access port between said upper cap and said lower port for crimping attachment of said biocompatible mesh material.

15. A percutaneous/subcutaneous access port for surgical implantation in the body of a mammal which does not require alignment for suturing/stapling through a preformed opening, such access port comprising a body portion defining a chamber with an open face, said body portion including a single layer of a non-porous biocompatible material attached to said body portion which substantially precludes the downgrowth of epidermal cells and which is sufficiently flexible whereby said subcutaneous access port may be fixed within a body via suturing or surgical stapling through any portion of said biocompatible material.

16. The percutaneous/subcutaneous access port of claim 15, wherein said non-porous biocompatible material comprises polymer film material or metallic film.

17. The percutaneous/subcutaneous access port of claim 16, wherein the biocompatible material comprises a polymer film material selected from the group consisting of a polysiloxane, a polytetrafluoroethylene, a polyester, a nylon, a polyolefin and a polyurethane.

18. The percutaneous/subcutaneous access port of claim 16, wherein the biocompatible material comprises a metallic film selected from the group consisting of stainless steel and titanium and has a thickness of about 0.0001–0.020 inches.

19. The percutaneous/subcutaneous access port of claim 16, wherein the biocompatible material comprises a metallic film selected from the group consisting of a stainless steel and titanium and has a thickness of about 0.002–0.010 inches.

20. The percutaneous/subcutaneous access port of claim 16, wherein the biocompatible material comprises a metallic film selected from the group consisting of a stainless steel and titanium and has a thickness of about 0.002–0.005 inches.

21. A percutaneous/subcutaneous access port for surgical implantation in the body of a mammal, such access port comprising a body portion defining a chamber with an open face, said body portion having attached thereto a biocompatible mesh material, whereby said subcutaneous access port may be fixed within a body via suturing or surgical stapling through said biocompatible mesh material, wherein said access port further contains a crimper on said access port for crimping attachment of said biocompatible mesh material.

22. The access port of claim 21, wherein said biocompatible mesh material is selected from the group consisting of synthetic polymeric fiber material, perforated film, and stainless steel.

23. The access port of claim 22, wherein said biocompatible mesh material comprises a synthetic polymer fiber material selected from the group consisting of polypropylene and poly(tetrafluoroethylene).

24. The access port of claim 22, wherein the biocompatible mesh material comprises a perforated film selected from the group consisting of polytetrafluoroethylene, stainless steel, and titanium.

25. The access port of claim 21, wherein said biocompatible mesh material is attached to said access port by an adhesive.

26. The access port of claim 25, wherein the adhesive is a biocompatible adhesive.

27. The access port of claim 26, wherein the adhesive is a silicon adhesive.

28. The access port of claim 21, wherein said access port comprises metallic material.

29. The access port of claim 21, wherein said access port comprises a non-metallic material.

30. The port of claim 21, wherein said biocompatible mesh material is disk-shaped and has a thickness in the range of about 0.005 to 0.060 inches, and a diameter in the range of about 0.10 to 4.0 inches.

31. The access port of claim 21, wherein the biocompatible mesh material has a pore size in the range of $1 \times 10^{-6}$ to 0.250 inches.

32. The access port of claim 21, wherein said access port comprises a non-metallic material.

33. The access port of claim 32, wherein said non-metallic access port comprises a plastic or elastomeric material.

34. A percutaneous/subcutaneous access port for surgical implantation in the body of a mammal, such access port comprising a body portion defining a chamber with an open face, said body portion having attached thereto a non-porous biocompatible material, whereby said subcutaneous access port may be fixed within a body via suturing or surgical stapling through said biocompatible material, wherein said non-porous biocompatible material comprises a biocompatible polymer film material or a biocompatible metallic film selected from the group consisting of stainless steel and titanium having a thickness of about 0.002–0.010 inches.

35. The percutaneous/subcutaneous access port of claim 34, wherein the biocompatible material comprises a polymer film material selected from the group consisting of a polysiloxane, a polytetrafluoroethylene, a polyester, a nylon, a polyolefin, and a polyurethane.

36. A percutaneous/subcutaneous access port for surgical implantation in the body of a mammal, such access port comprising a body portion defining a chamber with an open face, said body portion having attached thereto a non-porous biocompatible material, whereby said subcutaneous access port may be fixed within a body via suturing or surgical stapling through said biocompatible material, wherein said non-porous biocompatible material comprises a biocompatible polymer film material or a biocompatible metallic film selected from the group consisting of stainless steel and titanium having a thickness of about 0.002–0.005 inches.

37. The percutaneous/subcutaneous access port of claim 36, wherein the biocompatible material comprises a polymer film material selected from the group consisting of a polysiloxane, a polytetrafluoroethylene, a polyester, a nylon, a polyolefin and a polyurethane.

38. A method of providing repeated access to a preselected site within a patient by an external filament such as an external catheter, needle, wire or optional fiber, comprising the steps of:

providing a percutaneous/subcutaneous access port, said port comprising a body portion defining a chamber with an open face, said body portion having attached thereto a biocompatible mesh material, wherein said biocompatible mesh material consists essentially of a single layer of mesh material having a surface with pores therethrough, wherein said pores are of sufficient size and are present over the entirety of said biocompatible mesh material's surface to allow suturing or stapling through any portion of said mesh material, making an incision in a patient's skin, and locating said access port at a desired location and affixing said access port at said desired location via suturing or stapling through said mesh material, and closing the incision.

* * * * *

UNITED STATES PATENT AND TRADEMARK OFFICE
CERTIFICATE OF CORRECTION

PATENT NO. : 5,906,596
DATED : May 25, 1999
INVENTOR(S) : Tallarida

It is certified that error appears in the above-identified patent and that said Letters Patent is hereby corrected as shown below:

Claim 4, Col. 5 Line 60 "croup" should be --group--.

Signed and Sealed this

Twenty-third Day of May, 2000

Attest:

Q. TODD DICKINSON

Attesting Officer      *Director of Patents and Trademarks*